(12) United States Patent
Waller et al.

(10) Patent No.: US 11,859,208 B2
(45) Date of Patent: Jan. 2, 2024

(54) METHODS OF TREATING CANCER USING CELL BASED THERAPIES

(71) Applicant: Emory University, Atlanta, GA (US)

(72) Inventors: Edmund Waller, Atlanta, GA (US);
Anna Morris, Atlanta, GA (US);
Christopher Petersen, Atlanta, GA (US); Jian-Ming Li, Atlanta, GA (US);
Reema Panjwani, Bayside, NY (US);
Jingxia Li, Decatur, GA (US)

(73) Assignee: Emory University, Atlanta, GA (US)

( * ) Notice: Subject to any disclaimer, the term of this patent is extended or adjusted under 35 U.S.C. 154(b) by 162 days.

(21) Appl. No.: 16/092,068

(22) PCT Filed: Apr. 5, 2017

(86) PCT No.: PCT/US2017/026222
§ 371 (c)(1),
(2) Date: Oct. 8, 2018

(87) PCT Pub. No.: WO2017/176932
PCT Pub. Date: Oct. 12, 2017

(65) Prior Publication Data
US 2019/0144825 A1 May 16, 2019

Related U.S. Application Data

(60) Provisional application No. 62/319,957, filed on Apr. 8, 2016.

(51) Int. Cl.
| | | |
|---|---|---|
| *C12N 5/0783* | (2010.01) | |
| *A61K 45/06* | (2006.01) | |
| *A61K 38/48* | (2006.01) | |
| *A61K 35/17* | (2015.01) | |
| *A61P 35/00* | (2006.01) | |
| *A61K 38/20* | (2006.01) | |
| *A61K 39/39* | (2006.01) | |
| *A61P 31/00* | (2006.01) | |
| *A61K 35/28* | (2015.01) | |
| *A61K 38/22* | (2006.01) | |
| *A61K 38/54* | (2006.01) | |
| *C07K 16/28* | (2006.01) | |

(52) U.S. Cl.
CPC ............ *C12N 5/0638* (2013.01); *A61K 35/17* (2013.01); *A61K 35/28* (2013.01); *A61K 38/208* (2013.01); *A61K 38/22* (2013.01); *A61K 38/482* (2013.01); *A61K 38/4886* (2013.01); *A61K 38/54* (2013.01); *A61K 39/39* (2013.01); *A61K 45/06* (2013.01); *A61P 31/00* (2018.01); *A61P 35/00* (2018.01); *C07K 16/28* (2013.01); *C12N 5/0636* (2013.01); *C12Y 304/21039* (2013.01); *C12Y 304/24011* (2013.01); *C12N 2501/05* (2013.01); *C12N 2501/515* (2013.01)

(58) Field of Classification Search
CPC .... C12N 5/0638; C12N 5/0636; A61K 39/39; A61K 35/28; A61K 38/22; A61K 38/54; A61K 35/17; A61K 45/06; C07K 16/28; A61P 35/00
See application file for complete search history.

(56) References Cited

U.S. PATENT DOCUMENTS

| | | | |
|---|---|---|---|
| 6,534,055 B1 | 3/2003 | June et al. | |
| 7,754,482 B2 | 7/2010 | Riley | |
| 8,728,811 B2 | 5/2014 | Sagawa et al. | |
| 2004/0001829 A1* | 1/2004 | June | C07K 14/705 424/144.1 |
| 2004/0101519 A1 | 5/2004 | June | |
| 2005/0075290 A1* | 4/2005 | Gandhi | A61K 38/09 514/9.7 |
| 2010/0068192 A1 | 3/2010 | Enoki | |
| 2010/0150886 A1 | 6/2010 | Murui | |
| 2013/0302351 A1 | 11/2013 | Waller et al. | |
| 2015/0158925 A1 | 6/2015 | Waller | |
| 2015/0283178 A1* | 10/2015 | June | C07K 16/2803 424/85.2 |

FOREIGN PATENT DOCUMENTS

| | | | |
|---|---|---|---|
| JP | 2004267220 A | 9/2004 | |
| WO | 1994029436 A1 | 12/1994 | |

(Continued)

OTHER PUBLICATIONS

Anderson et al. Molecular and Cellular Biology, 20, 10, 2537-2551 (Year: 2010).*
Betjes Transpl Int Mar. 29(3):274-8, Sep. 8, 2015 (Year: 2016).*
Perkins et al. (Blood 126 (23): 1893 (Year: 2015).*
Balakrishnan et al. Leukemia 29, 1811-1822 (Year: 2015).*
Okkenhaug et al. Nature Review Immunology, 3, 317-330 (Year: 2003).*
Pearce et al. J Immunol. ; 195(7):3206-3217 (Year: 2015).*
Li et al. Cancer Res; 76(23), 6802-6815 (Year: 2016).*
Summerbell (Blood 122 (21): 1041, pp. 1-5 (poster) (Year: 2013).*
Fnu et al. Blood, vol. 138 1863 (Year: 2021).*
Li et al. PLoS One, 8(5), e63381, 1-14 (Year: 2013).*
Anderson et al. Vasoactive Intestinal Peptide Induces Cell Cycle Arrest and Regulatory Functions in Human T Cells at Multiple Levels, Molecular and Cellular Biology, 2010, 2537-2551.

(Continued)

*Primary Examiner* — Anoop K Singh
(74) *Attorney, Agent, or Firm* — Meunier Carlin & Curfman LLC (57) ABSTRACT

This disclosure relates to compositions and methods of reversing senescence in T cells by interrupting vasoactive intestinal peptide (VIP) signaling and/or inhibiting phosphatidylinositol-3-kinase (PI3 kinase) inhibitor signaling and uses in managing cancer and chronic viral infections. In certain embodiments, the disclosure contemplates methods of reversing T cell senescence by mixing T cell in vitro with an agent that prevents VIP from interacting with VIP receptors and/or a PI3 Kinase inhibitor. In certain embodiments, the disclosure contemplates the expansion of senescent T cells by mixing with a PI3 kinase inhibitor, an agent that block VIP and VIP receptor signaling, a VIP degrading enzyme, and combinations thereof.

13 Claims, 4 Drawing Sheets
Specification includes a Sequence Listing.

(56) References Cited

FOREIGN PATENT DOCUMENTS

| WO | 2012079000 | | 6/2012 | | |
| WO | 2012161755 | | 11/2012 | | |
| WO | WO-2012161755 | A2 * | 11/2012 | ............. | A61K 38/04 |
| WO | 2013126712 | | 8/2013 | | |
| WO | 2015104596 | | 7/2015 | | |
| WO | 2015142675 | A2 | 9/2015 | | |
| WO | WO-2015164745 | A1 * | 10/2015 | ............. | C12N 15/86 |
| WO | 2015188119 | A1 | 12/2015 | | |
| WO | 2016168595 | | 10/2016 | | |
| WO | 2016172583 | | 10/2016 | | |
| WO | 2016174652 | | 11/2016 | | |
| WO | WO-2017099712 | A1 * | 6/2017 | ............. | A61K 35/17 |

OTHER PUBLICATIONS

Busch et al. Role of memory T cell subsets for adoptive immunotherapy, Semin Immunol. 2016, 28(1): 28-34.

Delgado et al. The Significance of Vasoactive Intestinal Peptide in Immunomodulation, Pharmacol Rev 56:249-290, 2004.

He et al. Inhibition of tryptase and chymase inducednucleated cell infiltration by proteinase inhibitors, Acta Pharmacol Sin, 2004, 25 (12): 1677-1684.

Henson et al. Reversal of functional defects in highly differentiated young and old CD8 T cells by PDL blockade, Immunology, 2012, 135(4): 355-363.

Herman et al. Phosphatidylinositol 3-kinase-δ inhibitor CAL-101 shows promising preclinical activity in chronic lymphocytic leukemia by antagonizing intrinsic and extrinsic cellular survival signals, Blood, 2010, 116(12):2078-88.

Li et al. Pharmacological inhibition of VIP signaling enhances antiviral immunity and improves survival in murine cytomegalovirus-infected allogeneic bone marrow transplant recipients, Blood, 2013, 121(12):2347-51.

Li et al. Modulation of Immune Checkpoints and Graft-versus-Leukemia in Allogeneic Transplants by Antagonizing Vasoactive Intestinal Peptide Signaling, Cancer Res; 76(23), 1-14.

Moody et al. A vasoactive intestinal peptide antagonist inhibits non-small cell lung cancer growth, Proc. Natl. Acad. Sci. USA, 1993, vol. 90, 4345-4349.

Panjwani et al. T Cell Activation By Plasmacytoid Dendritic Cells Is Augmented By Inhibition of Vasoactive Intestinal Polypeptide Signaling: Implications for Cellular Immunotherapy, 2015, Ash 57th Annual Meeting & Exposition, Abstract 3438.

Petersen et al. Improving T-cell expansion and function for adoptive T-cell therapy using ex vivo treatment with PI3Kd inhibitors and VIP antagonists, Blood Adv, 2018, 2(3):210-223.

Rasmussen et al. Ex vivo expansion protocol for human tumor specific T cells for adoptive T cell therapy, Journal of Immunological Methods 355 (2010) 52-60.

Sharma et al. A Vasoactive Intestinal Peptide Antagonist Inhibits the Growth of Glioblastoma Cells, J Mol Neurosci, 2001, 17(3):331-9.

Teschner et al. In Vitro Stimulation and + Expansion of Human Tumour-Reactive cos Cytotoxic T lymphocytes by Anti-CD3/CD28/CD137 Magnetic Beads, Scand J Immunol, 2011, 74(2):155-64.

Topp et al. Restoration of CD28 Expression in CD28-CD8+ Memory Effector T Cells Reconstitutes Antigen-induced IL-2 Production, J Exp Med. 2003, 198(6): 947-955.

Vanderstegen et al. The pharmacology of second generation chimeric antigen receptors, Nat Rev Drug Discov. 2015, 14(7): 499-509.

Waller et al., Optimization of Ex Vivo Activation and Expansion of T Cells for Therapy of Lymphoma Via Antagonism of PI3K δ and Vasoactive Intestinal Peptide Signaling, Blood (2017) 130 (Supplement 1): 3195.

English translation of Office Action issued in Japanese Application No. 2018-552034 dated Dec. 8, 2020.

Suryadevara CM, Gedeon PC, Sanchez-Perez L, Verla T, Alvarez-Breckenridge C, Choi BD, Fecci PE, Sampson JH. Are BiTEs the "missing link" in cancer therapy? Oncoimmunology. Apr. 30, 2015;4(6):e1008339. doi: 10.1080/2162402X.2015.1008339. PMID: 26155413; Pmcid: PMC4485829.

Amelia Fernandez-Martin, Elena Gonzalez-Rey, Alejo Chorny, Doina Ganea, Mario Delgado Dr. Vasoactive intestinal peptide induces regulatory T cells during experimental autoimmune encephalomyelitis. European Journal of Immunology. vol. 36, Issue 2 p. 318-326.

G M Franconi, P D Graf, S C Lazarus, J A Nadel and G H Caughey. Mast cell tryptase and chymase reverse airway smooth muscle relaxation induced by vasoactive intestinal peptide in the ferret. Journal of Pharmacology and Experimental Therapeutics. Mar. 1989, 248 (3) 947-951.

Philippe Gourlet, André Vandermeers, Patrick Robberecht, Monique Deschodt-lanckman, Vasoactive intestinal peptide (VIP) and pituitary adenylate cyclase-activating peptide (PACAP-27, but not PACAP-38) degradation by the neutral endopeptidase EC 3.4.24.11, Biochemical Pharmacology, vol. 54, Issue 4, 1997, pp. 509-515.

Jones, and Janis Kuby. Kuby Immunology. 7th ed. New York: W.H. Freeman, 2013, p. 99-101; 3 pages.

Ortiz-Maldonado et al. .; "The biology behind PI3K inhibition in chronic lymphocytic leukaemia"; Ther Adv Hematol, 2015, vol. 6(1) 25-36; dated 2015; 12 pages.

Chen et al.; "Dual Inhibition of PI3K-Delta and Gamma By Duvelisib (IPI-145) Impairs CLL B- and T-Cell Migration, Survival and Proliferation in a Murine Xenograft Model Using Primary Chronic Lymphocytic Leukemia Cells"; Blood (2015) 126 (23) : 1753; dated Dec. 3, 2015; 3 pages.

Kane et al.; "The PI-3 kinase/Akt pathway and T cell activation: pleiotropic pathways downstream of PIP3"; Immunological Reviews 2003 vol. 192: 7-20; dated 2003; 14 pages.

English translation of office action issued in Chinese application No. 2022107521413, dated Jun. 29, 2023.

* cited by examiner

METHODS OF TREATING CANCER USING CELL BASED THERAPIES

CROSS-REFERENCE TO RELATED APPLICATIONS

This application is the National Stage of International Application No. PCT/US2017/026222 filed Apr. 5, 2017, which claims the benefit of U.S. Provisional Application No. 62/312,225 filed Apr. 8, 2016. The entirety of each of these applications is hereby incorporated by reference for all purposes.

STATEMENT REGARDING FEDERALLY FUNDED RESEARCH

This invention was made with government support under RO1 HL116737-01A and RO1 CA188523 awarded by the National Institutes of Health. The government has certain rights in the invention.

INCORPORATION-BY-REFERENCE OF MATERIAL SUBMITTED AS A TEXT FILE VIA THE OFFICE ELECTRONIC FILING SYSTEM (EFS-WEB)

The Sequence Listing associated with this application is provided in text format in lieu of a paper copy, and is hereby incorporated by reference into the specification. The name of the text file containing the Sequence Listing is 16094US_ST25.txt. The text file is 11 KB, was created on Oct. 8, 2018, and is being submitted electronically via EFS-Web.

BACKGROUND

Cytotoxic T cells directly kill cells, and the response is antigen specific. In order to destroy tumors, cytotoxic cells must proliferate in sufficient numbers to overtake the dividing cancer cells. However, T cells are considered senescent if they have limited proliferative potential in response to antigenic stimulation. Filaci et al. report that a subset of effector T-cells, CD8+ CD28− T regulatory lymphocytes, inhibit T cell proliferative and cytotoxic functions in human cancers. J Immunol, 2007, 179: 4323-4334. Montes et al. indicate that tumors induce senescent T cells as a potential form of tumor immune evasion. Cancer Res, 2008, 68: 870-879. Senescent T cells are characterized by the loss of CD27 and CD28 expression, lack of proliferative capacity, and increased expression of senescence-associated molecules. See Ramello et al. Cell Death and Disease, 2014. 5, e1507. Thus, there is a need to identify improved methods of treating cancer by reversing senescence in T cells.

Magnetic beads coated with anti-CD3 and anti-CD28 (anti-CD3/CD28 beads) have been reported for the expansion of T cells that has been used experimentally to boost T cell immunity in immunosuppressed cancer patients. See Porter et al. A phase 1 trial of donor lymphocyte infusions expanded and activated ex vivo via CD3/CD28 costimulation. Blood, 2006, 107:1325-1331.

Li et al report modulation of graft-versus-leukemia in allogeneic transplants by antagonizing vasoactive intestinal peptide signaling. Cancer Res, 2016, 76(23):6802-681. See also Li et al. PLoS One. 2013, 8(5):e63381; Li et al., Blood. 2013, 121(12):2347-51, Li et al., J Immunol. 2011, 187(2): 1057-65; U.S. Pat. No. 9,458,217; and U.S. Published Application number 2013/0302351.

References cited herein are not an admission of prior art.

SUMMARY

This disclosure relates to compositions and methods of reversing senescence in T cells by interrupting vasoactive intestinal peptide (VIP) signaling and/or inhibiting phosphatidylinositol-3-kinase (PI3 kinase) inhibitor signaling and uses in managing cancer and chronic viral infections. In certain embodiments, the disclosure contemplates methods of reversing T cell senescence by mixing T cell in vitro with an agent that prevents VIP from interacting with VIP receptors and/or the addition of a PI3 Kinase inhibitor. In certain embodiments, the disclosure contemplates the expansion of senescent T cells by mixing with a PI3 kinase inhibitor, an agent that block VIP and VIP receptor signaling, a VIP degrading enzyme, and combinations thereof.

In certain embodiments, the disclosure contemplates methods of stimulating isolated T cells or expanding senescent T cells by in vitro exposure of T cells to antibodies that bind CD3 and/or CD28 in combination with the PI3 kinase inhibitor, idelalisib, an agent that prevents VIP from interacting with VIP receptors, e.g. prevents signaling through the VIP receptor, a VIP degrading enzyme, and combinations thereof. In certain embodiments, the disclosure contemplates using anti-CD3 and anti-CD28 antibodies or binding agents optionally linked to a solid substrate such as magnetic beads.

In certain embodiments, the disclosure contemplates methods of proliferating T cells that are negative for CD28 and/or CD27 using an in vitro cell culture as disclosed herein providing replicated T cells that have increased expression of CD28 and/or CD27 compared with levels prior to replication.

In certain embodiments, the disclosure contemplates methods of proliferating T cells wherein prior to, during, or after proliferating the T cells, the T cells are mixed with a vector having a nucleic acid sequence encoding a chimeric antigen receptor, wherein the chimeric antigen receptor comprises cancer targeting sequence, a transmembrane domain, a T cell costimulatory molecule domain, and a signal-transduction component of a T-cell antigen receptor domain under conditions such that the cells express a chimeric antigen receptor on the surface of the cells.

In certain embodiments, the disclosure relates to in vitro cell culture compositions comprising a minimal essential medium and T cells and a VIP receptor antagonist, a PI3 kinase inhibitor, VIP-degrading enzyme, and combinations thereof and optionally further comprising anti-CD3 antibodies and anti-CD28 antibodies optionally immobilized on a solid substrate such as beads. In certain embodiments, the T cells are purified from bone marrow cells or blood cells.

In certain embodiments, the phosphatidylinositol-3-kinase inhibitor is selected from idelalisib, wortmannin, demethoxyviridin, perifosine, buparlisib, duvelisib, copanlisib, and alpelisib. In certain embodiments, the phosphatidylinositol-3-kinase inhibitor is selected from idelalisib in a culture at a concentration of greater than 0.001, 0.1, 1, 10, 100 nM or between 10 nM and 10 micromolar or between 10 nM and 500 nM, or between 10nM and 1 micromolar.

In certain embodiments, the culture comprises a VIP receptor antagonist such as VIPhyb comprising (SEQ ID NO: 1) KPRRPYTDNYTRLRKQMAVKKYLNSILN having a C-terminal amide. In certain embodiments, the culture comprises a VIP receptor antagonist such as VIPhyb in at a concentration of at least of added at 0.001, 0.01, 0.1, 0.5, 1.0, 2, or 3 micromolar. In certain embodiments, the culture comprises a VIP receptor antagonist such as VIPhyb in at a concentration of between 0.5 and 10 micromolar or between 1 and 8 micromolar.

In certain embodiments, the culture comprises an enzyme that hydrolyses VIP. In certain embodiments, the culture comprises a VIP degrading enzyme such as a peptidase, serine peptidase, a tryptase, chymase, human chymase 1 (CMA1), or chymotrypic serine proteinase. In certain embodiments, the culture has at least at least 0.001, 0.01, 0.1, or 1 microgram per mL of the VIP degrading enzyme such as a mast cell chymase. In certain embodiments, the disclosure contemplates a T cells culture comprising a minimal essential medium and isolated cells that express CD3 and/or CD4 and/or CD8 and are negative for CD27 and/or CD28 and a PI3 kinase inhibitor, agents that block VIP and VIP receptor signaling, and combinations thereof. The cells may be isolated by negative or positive selection using binding agents attached to solid supports such as beads, magnetic beads, or particles of fluorescent binding agents.

In certain embodiments, the anti-CD3 antibodies and anti-CD28 antibodies are immobilized on a bead, magnetic bead, or solid surface. In certain embodiments, more than 5.0% or 10% or 15% of the total cells in the culture express CD3 and/or CD4 and/or CD8. In certain embodiments, more than 20%, 25% or 50% of the total cells express CD3 and/or CD4 and/or CD8. In certain embodiments, more than 15% or 20% or 30% of the T cells in the culture are negative for CD28 and/or CD27. In certain embodiments, more than 20%, 25% or 50% of the T cells are negative for CD28 and/or CD27.

In certain embodiments, the purified T cells are obtained from centrifuging blood under conditions such that plasma and red blood cells separate providing purified T cells in a mixture of white blood cells between the plasma and red blood cells. In certain embodiments, the purified T cells are obtained by bone marrow aspirates or a bone marrow biopsy.

In certain embodiments, the purified T cells are obtained by mixing cells with a fluorescent marker that binds CD3 and purifying cells by fluorescent activated cell sorting. In certain embodiments, the purified T cells are obtained by mixing cells with a magnetized marker that binds CD3 and purifying cells by magnetic sorting. In certain embodiments, the purified T cells are obtained by mixing cells with a fluorescent marker that binds CD3 and/or CD4 and/or CD8 and purifying cells by fluorescent activated cell sorting. In certain embodiments, the purified T cells are obtained by mixing cells with a magnetized marker that binds CD3 and/or CD4 and/or CD8 and purifying cells by magnetic sorting.

In certain embodiments, the disclosure contemplates a solid substrate, such as beads, with anti-CD3 and anti-CD28 antibodies and having a VIP-degrading enzyme coupled to the surface. In certain embodiments, it is contemplated that the beads are arranged in the medium and the T cells are expanded on top of the medium such that the beads are sub-cellular.

In certain embodiments, the VIP degrading enzyme comprises human CMA1 Accession number GenBank: AAI03975.1:

(SEQ ID NO: 2)
MLLKLKEKASLTLAVGTLPFPSQFNFVPPGRMCRVAGWGRTGVLKPGSDT

LQEVKLRLMDPQACSHFRDFDHNLQLCVGNPRKTKSAFKGDSGGPLLCAG

VAQGIVSYGRSDAKPPAVFTRISHYRPWINQILQAN.

In certain embodiments, the VIP-degrading enzyme is human recombinant enkephalinase (neutral endopeptidase, EC 3.4.24.11) having (SEQ ID NO: 3)
DGICKSSDCIKSAARLIQNMDATTEPCTDFFKYACGGWLKRNVIPETSSR

YGNFDILRDELEVVLKDVLQEPKTEDIVAVQKAKALYRSCINESAIDSRG

GEPLLKLLPDIYGWPVATENWEQKYGASWTAEKAIAQLNSKYGKKVLINL

FVGTDDKNSVNHVIHIDQPRLGLPSRDYYECTGIYKEACTAYVDFMISVA

RLIRQEERLPIDENQLALEMNKVMELEKEIANATAKPEDRNDPMLLYNKM

TLAQIQNNFSLEINGKPFSWLNFTNEIMSTVNISITNEEDVVVYAPEYLT

KLKPILTKYSARDLQNLMSWRFIMDLVSSLSRTYKESRNAFRKALYGTTS

ETATWRRCANYVNGNMENAVGRLYVEAAFAGESKHVVEDLIAQIREVFIQ

TLDDLTWMDAETKKRAEEKALAIKERIGYPDDIVSNDNKLNNEYLELNYK

EDEYFENIIQNLKFSQSKQLKKLREKVDKDEWISGAAVVNAFYSSGRNQI

VFPAGILQPPFFSAQQSNSLNYGGIGMVIGHEITHGFDDNGRNFNKDGDL

VDWWTQQSASNFKEQSQCMVYQYGNFSWDLAGGQHLNGINTLGENIADNG

GLGQAYRAYQNYIKKNGEEKLLPGLDLNHKQLFFLNFAQVWCGTYRPEYA

VNSIKTDVESPGNFRIIGTLQNSAEFSEAFHCRKNSYMNPEKKCRVW.

In certain embodiments, cell cultures and methods described herein further include IL-12. In certain embodiments, the IL-12 is contemplated to enhance the effect of the VIP receptor antagonist on T cell proliferation stimulated in vitro with antibodies to CD3 and CD28.

In certain embodiments, the disclosure relates to expanding T cells, or expanding or reversing senescence in T cells, with a naturally occurring reactivity to cancer can be found infiltrated in tumors of the subject. The tumor can be harvested, and these tumor-infiltrating lymphocytes (TIL) can be expanded using methods discloses herein.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of immunology, medicine, organic chemistry, biochemistry, molecular biology, pharmacology, physiology, and the like, which are within the skill of the art. Such techniques are explained fully in the literature.

As described herein, the level of at least one protein based surface biomarker is measured in a biological sample from an individual. The protein level(s) may be measured using any available measurement technology that is capable of specifically determining the level of the biomarker in a biological sample. The measurement may be either quantitative or qualitative, so long as the measurement is capable of indicating whether the level of the biomarker in the biological sample is above or below the reference value.

Although some assay formats will allow testing of biological samples without prior processing of the sample, peripheral blood biological fluid samples may be processed prior to testing. Processing generally takes the form of elimination of cells (nucleated and non-nucleated), such as erythrocytes, leukocytes, and platelets in blood samples, and may also include the elimination of certain proteins, such as certain clotting cascade proteins from blood. In some examples, the peripheral biological fluid sample is collected in a container comprising EDTA.

The process of comparing a measured value and a reference value can be carried out in any convenient manner appropriate to the type of measured value and reference value for the biomarker at issue. As discussed above, measuring can be performed using quantitative or qualitative measurement techniques, and the mode of comparing a measured value and a reference value can vary depending on the measurement technology employed. For example, when a qualitative colorimetric assay is used to measure biomarker levels, the levels may be compared by visually comparing the intensity of the colored reaction product, or by comparing data from densitometric or spectrometric measurements of the colored reaction product (e.g., comparing numerical data or graphical data, such as bar charts, derived from the measuring device). However, it is expected that the measured values used in the methods of the disclosure will most commonly be quantitative values (e.g., quantitative measurements of concentration, such as nanograms of biomarker per milliliter of sample, or absolute amount). As with qualitative measurements, the comparison can be made by inspecting the numerical data, by inspecting representations of the data (e.g., inspecting graphical representations such as bar or line graphs).

It must be noted that, as used in the specification and the appended claims, the singular forms "a," "an," and "the" include plural referents unless the context clearly dictates otherwise. In this specification and in the claims that follow, reference will be made to a number of terms that shall be defined to have the following meanings unless a contrary intention is apparent.

As used herein the term "idelalisib" refers to the compound (S)-2-(1-(9H-purin-6-ylamino)propyl)-5-fluoro-3-phenylquinazolin-4(3H)-one or alternative salts thereof.

As used herein, "T cells that are negative for CD28 and/or CD27" refers to having low expression or lack expression of relative concentrations of these markers when compared to normal T-cells that express CD3 surface antigen markers in a healthy subject.

The term "fluorescence-activated cell sorting" or "FACS" refers to a method of sorting a mixture of cells into two or more areas, typically one cell at a time, based upon the fluorescent characteristics of each cell, a respectively applied electrical charge, and separation by movement through an electrostatic field. Typically, a vibrating mechanism causes a stream of cells to break into individual droplets. Just prior to droplet formation, cells in a fluid pass through an area for measuring fluorescence of the cell. An electrical charging mechanism is configured at the point where the stream breaks into droplets. Based on the fluorescence intensity measurement, a respective electrical charge is imposed on the droplet as it breaks from the stream. The charged droplets then move through an electrostatic deflection system that diverts droplets into areas based upon their relative charge. In some systems, the charge is applied directly to the stream, and the droplet breaking off retains charge of the same sign as the stream. The stream is then returned to neutral after the droplet breaks off. In other systems, a charge is provided on a conduit inducing an opposite charge on the droplet. Cells are typically made fluorescent by mixing the cell with antibody that specifically binds a marker that is made fluorescent by conjugation to a fluorescent molecule. However, other methods of making a cell fluorescent are contemplated such as by the use of molecular beacons.

A "minimal essential medium" refers a medium containing salts of calcium, magnesium, potassium, sodium, phosphate, and bicarbonate, vitamins, and essential amino acids. The 12 essential amino acids are: L-arginine; L-cystine; L-glutamine; L-histidine; L-isoleucine; L-leucine; L-methionine; L-phenylalanine; L-threonine; L-tryptophan; L-tyrosine; and L-valine. An MEM is often supplemented with components such as bicarbonate or glutamine. In certain embodiments, this disclosure contemplates a minimal essential medium supplemented with non-essential amino acids: L-ala; L-asn; L-asp; L-glu; L-gly; L-pro and L-ser. In certain embodiments, this disclosure contemplates a minimal essential medium supplemented with nucleosides (ribonucleosides and/or deoxyribonucleosides).

The term "recombinant" when made in reference to a nucleic acid molecule refers to a nucleic acid molecule that is comprised of segments of nucleic acid joined together by means of molecular biological techniques. The term "recombinant" when made in reference to a protein or a polypeptide refers to a protein molecule that is expressed using a recombinant nucleic acid molecule. The term recombinant nucleic acid is distinguished from the natural recombinants that result from crossing-over between homologous chromosomes. Recombinant nucleic acids as used herein are an unnatural union of nucleic acids from nonhomologous sources, usually from different organisms.

The terms "vector" or "expression vector" refer to a recombinant nucleic acid containing a desired coding sequence and appropriate nucleic acid sequences necessary for the expression of the operably linked coding sequence in a particular host organism or expression system, e.g., cellular or cell-free. Nucleic acid sequences necessary for expression in prokaryotes usually include a promoter, an operator (optional), and a ribosome-binding site, often along with other sequences. Eukaryotic cells are known to utilize promoters, enhancers, and termination and polyadenylation signals.

The terms "vasoactive intestinal peptide" and "VIP" refer to (SEQ ID NO: 12) HSDAVFTDNYTRLRKQMAVKKYLNSILN unless the context suggests otherwise. VIP is a multifunctional endogenous polypeptide that modulates both innate and adaptive immunity at multiple levels of immune cell differentiation and activation.

VIP is typically secreted by a variety of cells such as neurons (in both the central and peripheral nervous systems) B-cells, T-cells, and accessory cells. VIP and the closely related neuropeptide pituitary adenylyl cyclase-activating polypeptide (PACAP) bind to three known receptors—VPAC1, VPAC2, and PAC1. It is believed that T-cells and dendritic cells (DC) express VPAC1 and VPAC2, but not PAC1. PAC1 is mainly expressed on neuron and endocrine cells in the brain and pituitary and adrenal glands, and in most forms selectively binds PACAP.

The term "VIP antagonist" or "VIP receptor antagonist" refers to any molecule that inhibits or detracts from the ability of VIP to alter immune responses. VIP receptor antagonists are known including VIP analogues, VIP fragments, growth hormone-releasing factor analogs and hybrid peptides. A number of VIP receptor antagonists are disclosed in U.S. Pat. Nos. 5,565,424; 7,094,755; 6,828,304, and are all hereby incorporated by reference. Some examples of VIP receptor antagonist include [Ac-Tyr1,D-Phe2]GRF 1-29, amide, i.e., (SEQ ID NO: 4) YFDAIFTNSYRKVLGQL-SARKLLQDIMSR (Modifications: Tyr-1=N-terminal Ac, Phe-2=D-Phe, Arg-29=C-terminal amide); VIP (6-28), i.e., (SEQ ID NO:5) FTDNYTRLRKQMAVKKYLNSILN (Modifications: Asn-23=C-terminal amide); [D-p-Cl-Phe6, Leu17]-VIP, i.e., (SEQ ID NO:6) HSDAVFTDNYTRLRKQLAVKKYLNSILN (Modifications: Phe-6=p-Cl-D-Phe, Asn=C-terminal amide); VIP-hyb also known as VIPhybrid (SEQ ID NO: 1) KPRRPY-TDNYTRLRKQMAVKKYLNSILN, i.e., a hybrid peptide of neurotensin and VIP consisting of an N-terminal (SEQ ID NO:7) KPRRPY, also designated neurotensin (6-11)] followed by the C-terminal 22 amino acids of VIP, i.e., (SEQ ID NO:8) TDNYTRLRKQMAVKKYLNSILN, also designated VIP (7-28); N-terminal Stearyl, Norleucine 17 VIPhyb, i.e., (SEQ ID NO: 9) KPRRPY-TDNYTRLRKQXAVKKYLNSILN, wherein X is norleucine; Ac His1 [D-Phe(2), Lys(15), Arg(16), Leu(27)]-VIP (1-7)/GRF(8-27), i.e., (SEQ ID NO:10) HFDAVFTNSYRKVLKRLSARKLLQDIL, C-terminal amide; and pituitary adenylate cyclase-activating polypeptide, PACAP (6-38) C-terminal amide, i.e., (SEQ ID NO:11) TDSYSRYRKQMAVKKYLAAVLGKRYKQRVKNK . It is contemplated that any of these molecules may be modified with hydrocarbon or polyethylene glycol groups in order to provide improve properties such as solubility, bioavailability, and/or biological degradation.

As used herein, the terms "treat" and "treating" are not limited to the case where the subject (e.g., patient) is cured and the disease is eradicated. Rather, embodiments, of the present disclosure also contemplate treatment that merely reduces symptoms, and/or delays disease progression.

Immunophenotype of Patients with Relapsed Lymphoma

During physiologic aging and in individuals exposed to repeated rounds of chemotherapy or chronic inflammatory conditions, T-cells develop a condition of senescence in which they are anergic or have limited proliferative potential in response to antigenic stimulation. The phenotype of senescence T-cells has been described as those T-cells that lack co-stimulatory receptors CD27 and CD28 or have high levels of the CD57 marker. In addition, expression of PD1, a receptor for programmed death-ligand has been associated with the anergic state. The presence of anergic T-cells is a critical cofactor in the ability of patients to respond to vaccines or to mount protective and durable immune responses to chronic viral infections or cancer. Novel approaches to reverse T-cell senescence and anergy are needed to offer patients with chronic infections and cancer the prospect of effective cell based immunotherapy.

The immunophenotype of patients with relapsed lymphoma are characterized as having an over representation of T-cells with the anergic phenotype: CD3 positive, CD27 negative, CD28 negative. Whether signaling through the vasoactive intestinal polypeptide receptor contributed to T-cell senescence and antigen specific energy was performed. The addition of a peptide antagonist to VIP receptor called VIPhyb augmented T cell proliferation in vitro and mitigated the inhibitory effect of the native VIP peptide on T-cell proliferation.

Whether the addition of the VIPhyb antagonist could reverse the proliferative deficits of anergic T cells from patients with long-standing relapsed cancer was tested. The immunophenotype of T-cells in a patient with relapsed lymphoma was evaluated. There was a relative over representation of cells lacking the costimulatory receptor CD27 and CD28. In addition, the T cells from this station have high levels of CD57 expression, PD1 and Tim-3.

Using high-speed cell sorting subsets of T-cells were isolated defined by their levels of CD27 and CD28 expression from the patient with relapsed lymphoma and a healthy control. CD3 positive T-cells with each of the four phenotypes defined by CD27 and CD28 expression were sorted and cultured in vitro in the presence of anti-CD3/anti-CD28 beads. While total T-cells from healthy donors had 100% expression of the Ki67 proliferation marker following four days of culture, the corresponding total T-cell population from the patient with anergic T-cells following treatment for lymphoma had only 90% of T-cells expressing the Ki67 marker.

Following the daily addition of 3 uM VIPhyb to these cultures, the proportion of Ki67 positive T-cells from the anergic lymphoma patient was increased to 100%. Subsets of T-cells sorted on the basis of CD27 and CD28 expression from this patient showed that the CD27 positive, CD28 positive (double positive) population proliferated normally in response to anti-CD3/CD28 beads. In contrast, the T-cell subsets lacking expression of either CD27 or CD28 or both markers had impaired proliferated response when incubated with the anti-CD3/CD28 beads.

Addition of the antagonist VIPhyb augmented T-cell proliferation in the subsets lacking either CD27 or CD28. The addition of IL 12 to these cultures had a significant impact in increasing the proliferation fraction of T-cells that were CD28 negative but not those that were CD27 negative. Flow cytometry analysis of the T cells cultured with anti-CD3/anti-CD28 beads showed that the addition of 3 uM VIPhyb led to decreased levels of PD-1 expression compared with control cultures to which no VIP antagonist was added. This data indicates that VIP is induced during antigen specific activation of T-cells and that strategy to block VIP signaling could augment T-cell proliferation and reverse anergy among senescence T-cells from individuals with chronic inflammatory conditions or those who have been exposed to multiple cycles of chemotherapy.

Since the VIP peptide has a very short half-life in vivo of less than two minutes and is cleaved by endopeptidases, over expression of VIP specific peptidases in the vicinity of T-cells activated through their T-cell receptor are believed to result in augmented activation and proliferation of T-cells and could reverse immune senescence.

Methods of Therapeutic Use

In certain embodiments, the disclosure contemplates an in vivo method of reversing T cell senescence by infusing, implanting, or administering an effective amount of anti-CD3 antibodies and anti-tumor antibodies and a recombinant mast cells chymase. In certain embodiments, the recombinant mast cells chymase is administered or infused intravenously into a subject/patient receiving anti-CD3 antibodies and an antibody to a tumor-associated antigen.

In certain embodiments, the disclosure contemplates methods of treating cancer or a chronic infection comprising: purifying T cells from a subject providing isolated T cells; mixing the isolated T cells with anti-CD3 antibodies and anti-CD28 antibodies optionally immobilized on a bead or solid surface in combination with a PI3 kinase inhibitor, a VIP receptor antagonist, a VIP degrading enzyme, or combinations thereof; under conditions such that the T cells replicate providing replicated T cells have increased expression of CD28 compared with levels prior to replication; and administering an effective amount of the replicated T cells to a subject in need thereof.

In certain embodiments, the disclosure contemplates methods of treating cancer comprising: purifying T cells from a subject providing isolated T cells; mixing the isolated T cells with anti-CD3 antibodies and anti-CD28 antibodies optionally immobilized on a bead or solid surface in combination with a PI3 kinase inhibitor, a VIP receptor antagonist, a VIP degrading enzyme, or combinations thereof; under conditions such that the T cells replicate providing replicated T cells have increased expression of CD28 compared with levels prior to replication; and administering an effective amount of the replicated T cells to a subject in need thereof. In certain embodiments, the replicated T cells express a chimeric antigen receptor on the surface of the cells. In certain embodiments, the method further comprises administering a PI3 kinase inhibitor, a VIP receptor antagonist, a VIP degrading enzyme, or combinations thereof, before, during, or after administering the replicated T cells.

In certain embodiments, the disclosure contemplates method of treating cancer comprising: purifying T cells from a subject providing isolated T cells; culturing the isolated T cells by in vitro exposure of T cells to antibodies that bind CD3 and/or CD28 in combination with the PI3 kinase inhibitor, idelalisib, an agent that prevents VIP from interacting with VIP receptors, e.g. prevents signaling through the VIP receptor, a VIP degrading enzyme, and combinations thereof providing expanded T cells with an increased expression of CD28; and administering an effective amount of the expanded T cells to the subject.

In certain embodiments, the disclosure contemplates method of treating cancer comprising administering an effective amount of a bi-specific antibody in combination with a VIP receptor antagonist and/or a phosphatidylinositol-3-kinase inhibitor to a subject in need thereof, wherein the bi-specific antibody comprises a cancer targeting binding sequence and a CD3 binding sequence. In certain embodiments, the bi-specific antibody is catumaxomab or blinatumomab.

In certain embodiments, the disclosure contemplates methods of treating cancer with a combination of bi-specific antibodies or anticancer antibody or antibody to a tumor associated antigen and administration or parental administration of a VIP receptor antagonist such as VIPhyb. In certain embodiments, the anti-tumor specific antibody is directed to CD19. In certain embodiments, the anti-cancer antibody is directed to CD123. In certain embodiments, the anti-cancer antibody is directed to HER2/neu. In certain embodiments, the anti-cancer antibody is directed to BMCA, a myeloma associated antigen. In certain embodiments, the anti-cancer antibody is directed to EGFR. In certain embodiments, the anti-cancer antibody is directed to PD-L1 or PD1.

In certain embodiments, the disclosure contemplates methods of treating cancer comprising administering an effective amount of cells having a chimeric antigen receptor in combination with a VIP receptor antagonist or phosphatidylinositol-3-kinase inhibitor to a subject in need thereof, wherein the chimeric antigen receptor comprises cancer targeting sequence, a transmembrane domain, a T cell costimulatory molecule domain, and a signal-transduction component of a T-cell antigen receptor domain.

In certain embodiments, the disclosure contemplates in vivo methods of reversing senescence of T cells comprising genetically modifying T cells to express on their surface a VIP degrading enzyme. In certain embodiments, the VIP degrading enzyme is recombinant human CMA1 mast cell chymase. In certain embodiments, the genetically modified T cells also express a chimeric antigen receptor that targets them to cancer cells. In certain embodiments, the genetically modified T cells are administered or infused into a subject with cancer.

In certain embodiments, this disclosure relates to methods of treating cancer comprising: purifying T cells from a subject that express a T cell receptor wherein the T cells express CD3 and optionally CD4 and/or CD8 providing isolated T cells; mixing the isolated T cells with cell culture disclosed herein under conditions such that the cells expand, and implanting or administering an effective amount of the expanded cells into the subject.

In certain embodiments, the disclosure contemplates methods of treating cancer comprising administering T cells comprising a vector configured to express a chimeric antigen receptor, e.g., the cells has been infected with a recombinant virus that has a nucleic acid that codes a chimeric antigen receptor, in combination with administration of a VIP receptor antagonist such as VIPhyb, a VIP-degrading enzyme, a PI3 inhibitor, or combinations thereof.

In certain embodiments, the disclosure contemplates methods of treating cancer comprising: purifying cells from a subject that express CD3 and/or CD4 and/or CD8 providing isolated T cells; measuring the expression of CD27 and/or CD28, on the isolated T cells providing measured values of CD27 and/or CD28; comparing the measured values of CD27 and/or CD28, to a reference level, and if the measured levels of CD27 are lower than normal and/or the measured levels of CD28 are lower than normal, then administering an effective amount of a VIP receptor antagonist, a VIP-degrading enzyme, a PI3 inhibitor, or combinations thereof to a subject.

In certain embodiments, the disclosure contemplates methods of treating cancer comprising purifying cells from a subject that express CD3 and/or CD4 and/or CD8 providing isolated T cells; measuring the expression of CD27 and/or CD28, on the isolated T cells providing measured values of CD27 and/or CD28; if the measured values of CD27 is lower than normal and/or the measured value of CD28 is lower than normal providing replicated T cells then mixing the isolated T cells with a VIP receptor antagonist a VIP-degrading enzyme, a PI3 inhibitor, or combinations thereof under conditions such that the isolated T cells replicate; and implanting or administering an effective amount of the replicated T cells into the subject optionally in combination with administering a VIP receptor antagonist, a VIP-degrading enzyme, a PI3 inhibitor, or combinations thereof to the subject.

In certain embodiments, the disclosure relates to expanding T cells that are positive for CD3 and negative for CD4 and CD8 such as gamma delta T cells (γδ T cells). Gamma delta T cells that have a distinctive T-cell receptor (TCR) on their surface. Most T cells are αβ (alpha beta) T cells with TCR composed of two glycoprotein chains called α (alpha) and β (beta) TCR chains. In contrast, gamma delta (γδ) T cells have a TCR that is made up of one γ (gamma) chain and one δ (delta) chain.

In certain embodiments, the disclosure contemplates a T-cell genetically modified to express on their surface a VIP-degrading enzyme. In certain embodiments, the VIP-degrading enzyme is recombinant human CMA1 mast cell chymase. In certain embodiments, the genetically modified T cells also express a chimeric antigen receptor that targets them to cancer cells. In certain embodiments, the genetically modified T cells are administered or infused into a human subject with cancer.

In certain embodiments, this disclosure relates to methods of treating cancer comprising administering an effective amount of a bi-specific antibody in combination with a VIP receptor antagonist, a PI3 kinase inhibitor, VIP-degrading enzyme, and combinations thereof. In certain embodiments, the bi-specific antibody is catumaxomab. In certain embodiments, the subject is diagnosed with malignant ascites. In certain embodiments, the bi-specific antibody is blinatumomab. In certain embodiments, the cancer is leukemia.

In certain embodiments, the disclosure contemplates methods of treating cancer comprising: purifying and expanding T cells using methods provided herein providing isolated T cells; mixing the isolated T cells with bi-specific antibodies under conditions such that the bispecific antibodies bind the CD3-T cell receptor complex; and administering an effective amount of the bispecific antibody bound T cells to the subject in combination with administering a VIP receptor antagonist, a PI3 kinase inhibitor, VIP-degrading enzyme, and combinations thereof to a subject in need thereof.

Bi-specific antibodies contain two targeting sequences, the first targets a tumor-associated antigen and the second targets the CD3 T-cell receptor complex such that T-cells can engage cancer cells. The Bi-specific antibody is linking the T cells to the cancer cells. See Zhukovsky et al. Bispecific antibodies and CARs: generalized immunotherapeutics harnessing T cell redirection, Current Opinion in Immunology, 2016, 40: 24-35. In certain embodiments, this disclosure contemplates that the bi-specific antibody is directed to the tumor-associated antigen, CD19 epitope, CD123, HER2/neu, or a BMCA, a myeloma associated antigen.

In order to improve the ability of immune cells to kill cancerous cells, T cells can be isolated from the blood of a patient and genetically altered to express chimeric antigen receptors to specifically target proteins expressed on the surface of cancerous cells and stimulate an immune response. When put back into the patient, the cells attack the cancerous cells. In certain embodiment, this disclosure contemplates using CAR T cells that target the CD22 and/or CD19 antigens. CD19 is a protein expressed on cancerous B cells. Brentjens et al. report that T cells altered to bind CD19 can induce remissions of cancer in adults with chemotherapy-refractory acute lymphoblastic leukemia. Sci Transl Med, 2013, 5(177):177ra38.

In a typical procedure, T cells are purified and isolated from blood or bone marrow. For example, T cells are collected via apheresis, a process that withdraws blood from the body and removes one or more blood components (such as plasma, platelets or other white blood cells). The remaining blood is then returned back into the body. The cells are exposed to a recombinant vector, such as a lentiviral vector, that infects the cells in a way that a CAR protein is produced to be present in the cell membrane. The T cells may be sent to a laboratory or a drug manufacturing facility where they are genetically engineered to produce chimeric antigen receptors (CARs) on their surface. Before and/or after infecting the isolated cells with the recombinant vector, the cells may be induced to replicate using methods disclosed herein. The genetically modified T cells may be expanded by growing cells in the laboratory until there are sufficient number of them. Optionally, these CAR T cells are frozen. The modified cells are then administered back to the patient. In certain embodiments, this disclosure contemplates that the subjects are administered with a VIP receptor antagonist, VIP-depredating enzyme, and/or an IP3 kinase inhibitor optionally in combination with one or more chemotherapy agents before they receive the infusion of CAR T cells.

In certain embodiments, the disclosure relates to cells made by processes disclosed herein that contain recombinants vector comprising a nucleic acid that encodes a chimeric polypeptide comprising a targeting sequence, a transmembrane domain, a T cell costimulatory molecule domain, and a signal-transduction component of a T-cell antigen receptor domain.

In certain embodiments, the targeting sequence in a chimeric antigen receptor refers to any variety of polypeptide sequences capable of selectively binding to a surface protein on target cells, e.g., cancer cells. Other targeting sequences may be variable binding regions of antibodies, single chain antibodies, and antibody mimetic. In certain embodiments, targeting is achieved via a single-chain variable fragment (scFv) derived from a monoclonal antibody. The targeting sequence it typically connected to the intracellular domains by a hinge/transmembrane region, commonly derived from CD8 or IgG4. The intracellular domains may contain co-stimulatory domains such as 4-1BBzeta and/or CD28zeta linked to the cytoplasmic signaling domain of CD3zeta.

EXAMPLES

VIP Signaling Regulates T-Cell Proliferation Induced by Allo-Antigen

Figure 1A:
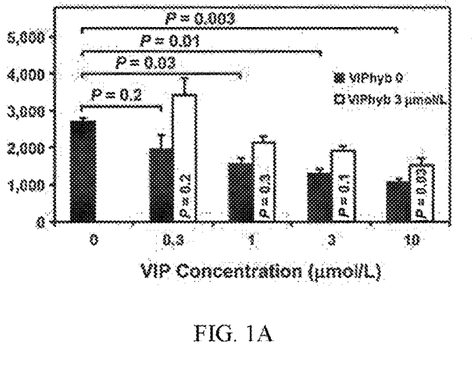
FIG. 1A shows data indicating VIPhyb treatment augmented in vitro T-cell proliferation stimulated by alloantigen. Proliferation of luciferase B6 splenic T cells cultured for 3 days in MLR with irradiated FVB splenocytes, with daily addition of VIP and/or VIPhyb to achieve the concentrations shown (0-10 mmol/L).
Figure 1B:
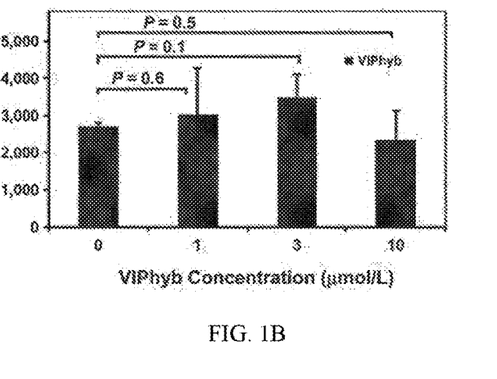
FIG. 1B shows data for variant concentrations of VIPhyb.

To explore the role of VIP signaling in allo-immune responses, one-way mixed lymphocyte reactions (MLR) were performed containing VIP and/or the antagonistic VIPhyb peptide. Addition of VIP decreased Luciferase T-cell proliferation in a dose-dependent manner, while adding VIPhyb increased T-cell proliferation. VIPhyb reversed the suppressive effect of VIP in MLR, restoring T-cell proliferation to higher levels than control cultures.

Pharmacological Blockade During Ex Vivo T Cell Expansion for CAR T Manufacture Increases Yield and Preserves the Naïve and Central Memory Compartments Diffuse large B cell lymphoma (DLBCL) is an aggressive B cell malignancy that mainly affects older patient populations. Despite the robust treatment regimens available, a subset of DLBCL patients exists with lymphoma that is highly treatment-resistant. Due to the fact that these patients disease are refractory to virtually all of the current treatment regimens, CAR T therapy holds tremendous promise as an effective salvage option, however many patients have failed to receive treatment in clinical trials due to a failure of ex vivo T cell expansion. This failure is due in large part to the damage done by numerous rounds of therapies as well as the age of the patients. Additionally, data indicates that patients with NHL have a skewed ratio of memory to naïve T cells resulting in impaired cellular immunotherapy.

Two of the surface proteins that are indicative of a patient's potential for successful T cell expansion are CD27 and CD28. T cells that express both CD27 and CD28 have the greatest proliferative potential while T cells that lack expression of both often do not expand and die during anti-CD3/CD28 activation and expansion. Healthy individuals have an abundance of CD27+CD28+ (double positive) T cells while patients with DLBCL have an over-abundance of CD27−CD28− (double negative) T cells. This over-representation of the double negative population in lymphoma patients helps to further explain the failure of the T cells to adequately expand during CAR T manufacture. In addition to the lack of CD27 and CD28 expression, DLBCL patient T cells also exhibit signs of exhaustion and senescence that both lead to functional impairments and the inability to expand.

To address the issues with DLBCL patient T cell expansion during CAR T cell manufacture, a variety of technologies were utilized in order to enhance expansion of specific desired T cell populations. Inclusion of the PI3K δ inhibitor idelalisib alone or in combination with a mast cell chymase or antagonist of vasoactive intestinal peptide (VIPhyb) during T cell activation increases the number of viable T cells obtained and increases the proportion of naïve and central memory cells. Naïve and central memory cells are the most effective subset for adoptive cellular immunotherapy. Additionally, inclusion of either idelalisib or VIPhyb increases the frequency of CD27+CD28+ cells while decreasing the frequency of CD27−CD28− cells. Further studies using murine and human T cells have indicated that while blockade of PI3K δ has an inhibitory effect on proliferation, the prevention of terminal differentiation and the preservation of the naïve compartment enhance T cell survival and yield. This data indicates that the culture conditions used not only increase the number of total patient T cells, but also preserve the compartments most effective in adoptive T cell immunotherapy. As such, utilization of our methods during CAR T manufacture has the potential to enable the development of the last-resort treatment that many DLBCL patients have previously been unable to receive.

Expansion of Senescent T Cells with P13 Kinase Inhibitors and Blocking VIP Signaling Idelalisib is an inhibitor of PI3 kinase. PI3 kinase is an important signaling pathway for lymphocyte activation and differentiation, and regulates AKT and mTOR1 activity. Idelalisib is FDA-approved for treatment of patients with chronic lymphocytic leukemia and indolent B cell malignancy. Patients treated with idelalisib have been noted to have continued anti-cancer responses after drug treatment has stopped and to develop auto immune-like signs and symptoms including colitis and rash, leading to the hypothesis that idelalisib modulates the immune system and activates or preserves Th1-polarized T cells.

Idelalisib treatment leads to increased T-cell activation in patients with CLL. Ex vivo exposure of activated T cells to idelalisib potentiate their activation and in vitro expansion. By adding a range of idelalisib concentrations to T cells cultured in vitro with anti-CD3/CD28 beads, T cell expansion and differentiation was measured.

A T cell sample that was used from a patient with lymphoma who had senescent T cells that failed to expand in vitro when manufacturing of CAR T cell was attempted. Monocytes were depleted from the T cell sample, as monocytes are known to inhibit T cell expansion in cultures containing anti-CD3/CD28 beads. The effect of a range of idelalisib concentrations were compared alone and in combination with 3 uM VIP peptide antagonist (VIPhyb) or 1 ug/ml mast cell chymase, an enzyme that degrades endogenous VIP on T cell activation, differentiation and proliferation. Numbers of viable T cells were measured during a 10 day in vitro cultures as well as the T cell differentiation and activation profiles, focusing on the relative numbers of T cells with a senescent phenotype in which co-stimulatory receptors CD27 and CD28 are both absent (CD27– CD28–), to an activated phenotype, in which either CD27, CD28, or both co-stimulatory receptors are present (CD27+CD28+).

Aliquots of frozen patient apheresis products or PBMC from ficolled whole blood were rapidly thawed and rested overnight in complete RPMI 1640 supplemented with 10% fetal bovine serum, 100 U/mL penicillin, 100 µg/mL streptomycin, and 50 µM 2-mercaptoethanol (complete media). The following day, red blood cells were removed from apheresis products by ficoll gradient. The leukocytes were then enriched for T cells using an EasySep human T cell enrichment kit according to manufacturer's instructions. Cells were plated in 200 µL of complete media in each well of a 96 well flat-bottom plate. Compounds were added at the indicated concentrations, and the DMSO concentration was normalized to 0.1% for all wells. Anti-CD3/CD28 beads were added at a 1:1 bead:cell ratio. On day 7 post-stimulation, cells from each treatment were transferred to new media. Fresh compounds and beads were then added, and the cells were cultured for an additional 3 days. On day 10 post-initial stimulation, the beads were removed, and the cells were stained for flow cytometric analysis.

Cells were washed twice in PBS. The cells were also stained using a fixable viability dye. Surface markers were then stained by adding fluorochrome-conjugated antibodies to CD3, CD4, CD8, CD27, CD28, CD45RA, CD45RO, PD-1, and CCR7. To assess proliferation, half the cells were evaluated for expression of Ki67. Ki67 staining was performed using a FoxP3 intracellular staining kit. Just prior to running samples, Accucheck counting beads were added to each tube. Samples were acquired on a BD FACS Aria, and analysis was performed using FlowJo software. Viable cells were used in the analysis. The absolute numbers of cells was calculated for each population according to instructions provided by the manufacturer of the Accucheck counting beads.

Figure 2:
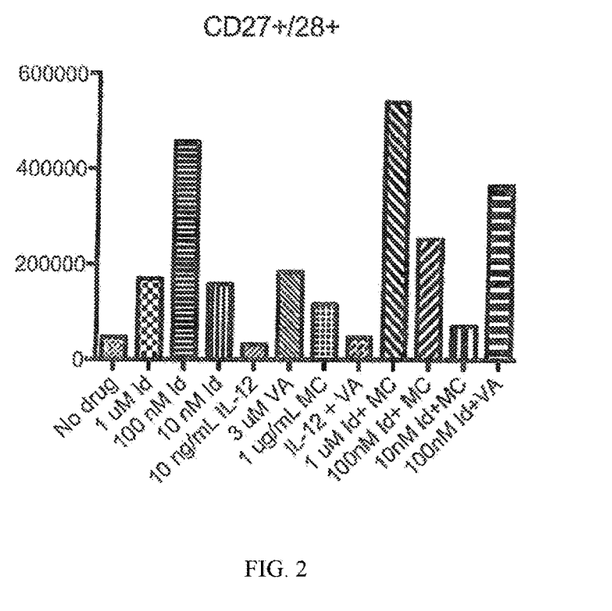
FIG. 2 shows data on the relative number of CD27+ and CD28+ cells produced in an in vitro culture on a sample wherein the patient has senescent T cells. "Id" refers to idelalisib. "VA" refers to VIPhyb. "MC" refers to human mast cell chymase (CMA1).
Figure 3A:
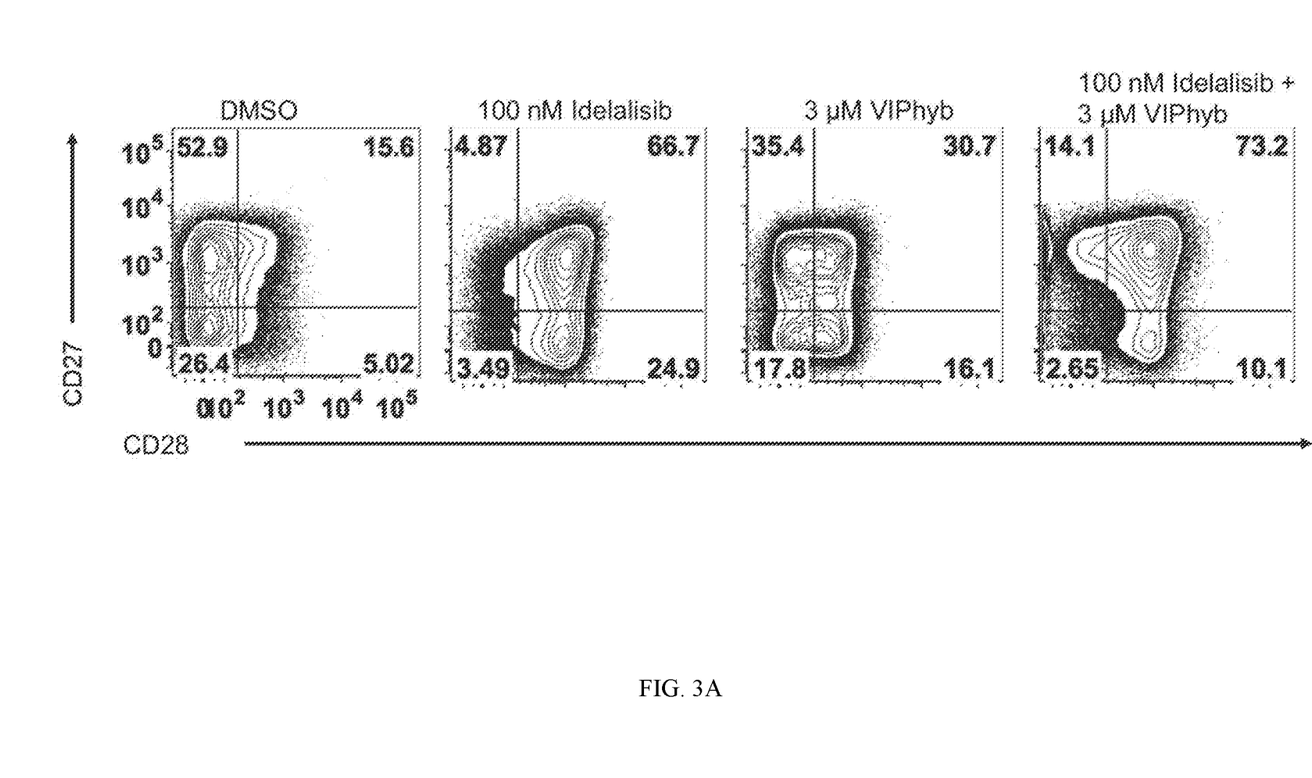
FIG. 3A shows data on the expression of CD27 and CD28 on the total CD3+ population on day 14 of expansion. DLBCL patient T cells were expanded for 14 days with CD3/CD28 beads in the presence of 30 U/mL IL-2 with or without the indicated compounds.
Figure 3B:
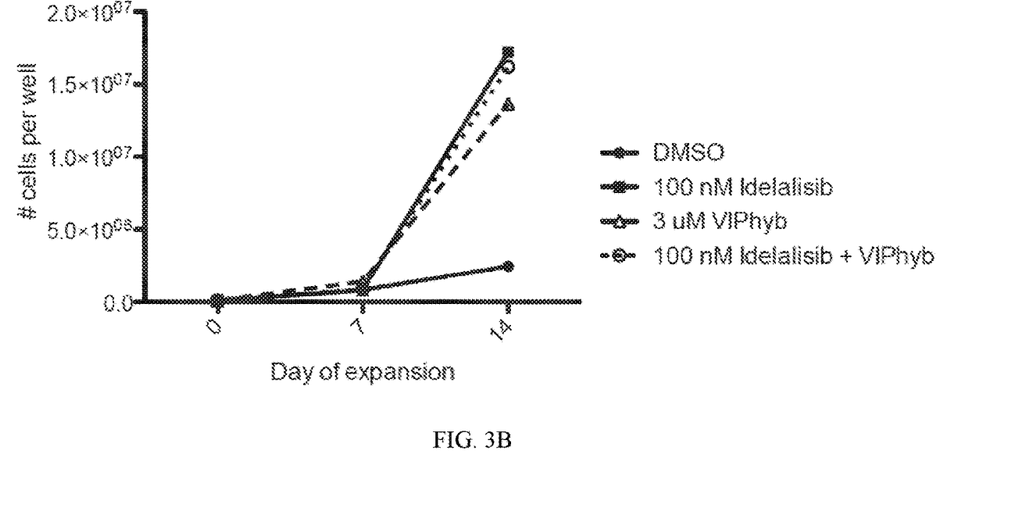
FIG. 3B shows an expansion curve of patient T cells in the presence or absence of the indicated compounds. The preservation of the CD27+CD28+ compartment and increased overall yield in a DLBCL patient T cell expansion with Idelalisib and VIPhyb.
Figure 4:
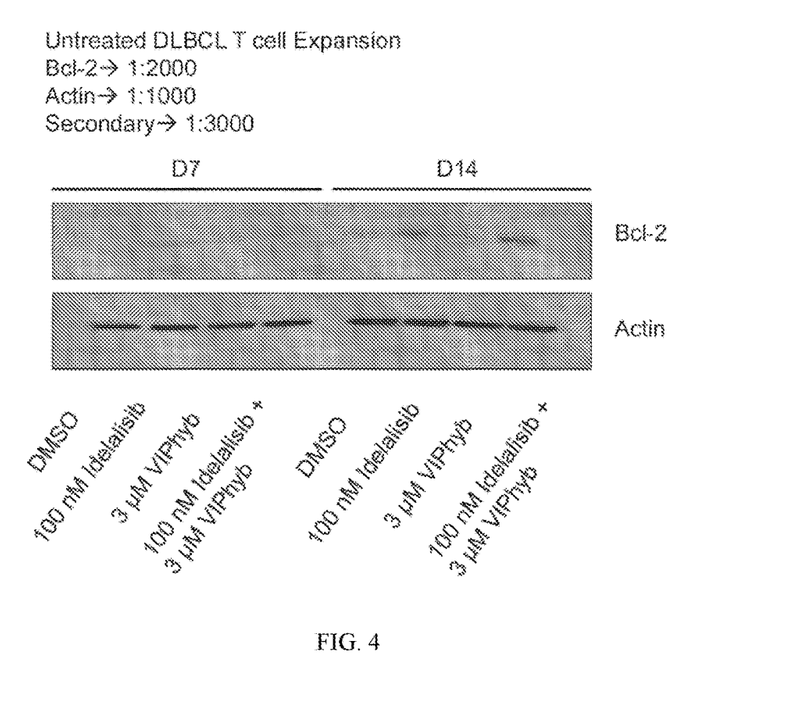
FIG. 4 shows data indicating the expression of Bcl-2 in lymphoma patient T cells is increased with the addition of VIPhyb, Idelalisib, or a combination of both. Protein lysates from patient T cell expansion cultures were prepared on days 7 and 14. Samples were run on an SDS-PAGE gel prior to transfer to a nitrocellulose membrane. The membrane was then probed for the pro-survival Bcl-2 protein, stripped, and then re-probed for actin as a loading control.
Figure 5A:
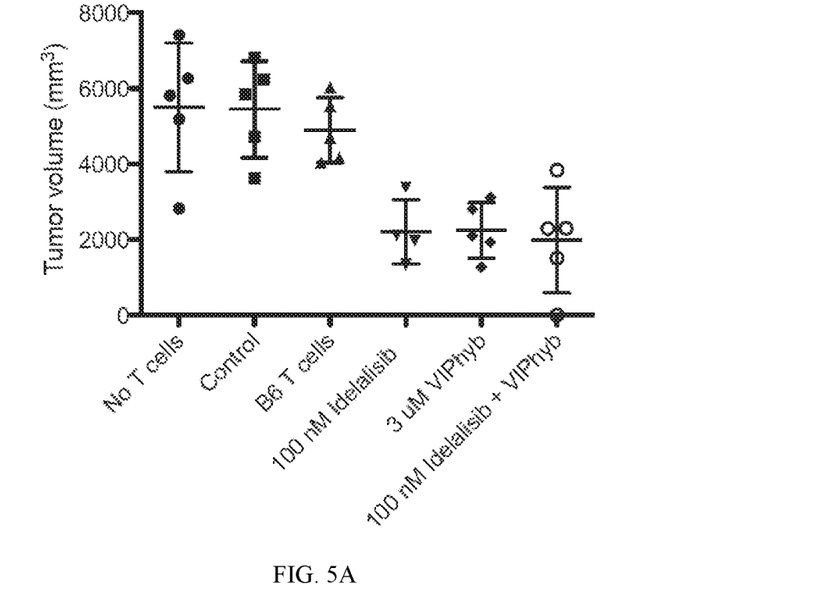
FIG. 5A shows data on tumor volumes on day 18 post-tumor cell injection. Mice were injected subcutaneously with $5 \times 10^5$ E.G7-OVA cells which were allowed to grow for 7 days until a palpable tumor formed. During this period, OT-I, OT-II, and B6 T cells were expanded with CD3/CD28 beads in the presence of IL-2 and the indicated compounds for 3 days. On day 7 of tumor growth, mice were injected intravenously with a combination of expanded OT-I, OT-II, and B6 T cells ($2 \times 10^6$ OT-I, $1 \times 10^6$ OT-II, and $2 \times 10^6$ B6 cells) or $2 \times 10^6$ B6 T cells as a control. Mice were then monitored for tumor growth which was calculated as $(L \times W2)/2$.
Figure 5B:
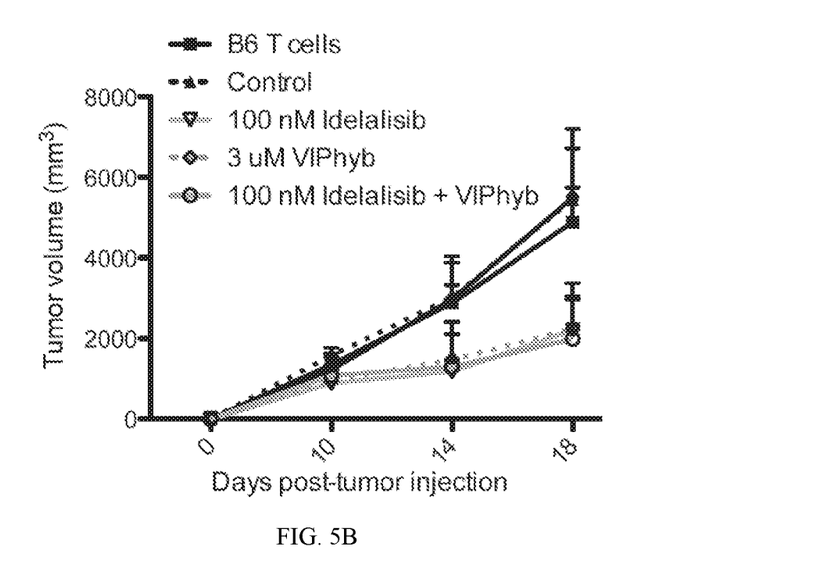
FIG. 5B shows tumor growth curve showing the rate of growth among groups over time. Expansion of mouse T cells in the presence of Idelalisib, VIPhyb, or a combination of both enhances their therapeutic efficacy in an OVA-expressing lymphoma model.

The addition of idelalisib to the T cell cultures at concentrations of 1 uM or 100 nM, significantly increased the proportion of T cells co-expressing CD27 and CD28 compared to control cultures with no added drug. Of note the fraction of senescent T cells that lacked both CD27 and CD28 costimulatory receptors was decreased from 55.2% in control cultures with no added drug, to 16.1% in cultures with 10 nM idelalisib, 35.7% in cultures with 3 uM VIPhyb, and 37.4% in cultures with 1 µg per ml mast cell chymase.

Idelalisib at 100 nM concentration was synergistic in enhancing the proportion of T cells expressing co-stimulatory receptors when combined with VIPhyb or chymase, with the fraction of CD27+CD28+ cells 21.5% with the combination of 100 nM idelalisib and VIPhyb and 14.2% in the combination of 100 nM idelalisib and chymase versus to 3.5% in control cultures with no added drug.

Numbers of effector memory T cells (Tem) in the 10-day cultures were also increased by exposure to idelalisib, VIPhyb and the combinations of idelalisib with chymase and VIPhyb. The total numbers of viable T cells in cultures was significantly increased with combinations of idelalisib and chymase or idelalisib and VIPhyb compared with control cultures with no added drug. Of note, the total numbers of CD27+ CD28+ T cell subset were enriched more than 10-fold in the cultures containing 100 nM idelalisib, 1 uM idelalisib plus 1 ug/ml chymase, or 100 nM idelalisib plus 3 uM VIPhyb compared with cultures containing no added drugs, while total numbers of CD3+ Tem in the 10-day cultures were increased 10-fold in cultures containing 1 uM idelalisib plus chymase compared with control cultures with no added drugs. CD3+ central memory T cells (Tcm) were increased 5-10 fold in cultures containing idelalisib alone, VIPhyb alone, chymase alone, or combinations of idelalisib with either VIPhyb or chymase compared with control cultures with no added drugs.

This data indicates that senescent T cells that cannot be expanded in culture with anti CD3/CD28 beads and that failed to yield sufficient manufactured CAR T cells for clinical use can be significantly expanded in vitro with the addition of idelalisib, VIPhyb or mast cell chymase as single agents or in combination, These results support the addition of these agents during CAR T manufacturing and support their use in vitro to expand senescent T cells to enhance cancer immunotherapy and anti-viral immunity.

The invention claimed is:

1. An in vitro method of replicating anergic T cells, said method comprising
culturing an isolated CD28⁻CD27⁻ anergic T cells in a medium containing an effective amount of anti-CD3 antibodies and anti-CD28 antibodies in combination with a phosphatidylinositol-3-kinase inhibitor and a vasoactive intestinal peptide (VIP) receptor antagonist for a sufficient time to produce CD28⁺CD27⁺ and/or CD28⁺CD27⁻ replicated T cells having increased expression of CD28 compared with levels prior to replication, thereby providing replicated T cells.

2. The method of claim 1, wherein the replicated CD28+ CD27+ and the replicated CD28+CD27− T cells express a chimeric antigen receptor on the surface of the cells.

3. A method of treating a cancer in a subject, said method comprising:
(i) purifying T cells from the subject providing isolated anergic T cells, wherein the isolated anergic T cells are CD28⁻CD27⁻ T cells;
(ii) culturing the isolated CD28⁻CD27⁻ anergic T cells in a medium containing an effective amount of anti-CD3 antibodies and anti-CD28 antibodies in combination with a phosphatidylinositol-3-kinase inhibitor and a vasoactive intestinal peptide (VIP) receptor antagonist for a sufficient time to produce CD28⁺CD27⁺ replicated T cells having increased expression of CD28 compared with levels prior to replication; and
(iii) administering an effective amount of the CD28+ CD27+ replicated T cells from step (ii) to the subject, thereby treating the cancer, and wherein the cancer is leukemia or lymphoma.

4. The method of claim 3, wherein the CD28+CD27+ replicated T cells express a chimeric antigen receptor on the surface of the cells.

5. The method of claim 3, further comprising administering a PI3 kinase inhibitor to the subject before, during, or after administering the CD28+CD27+ replicated T cells.

6. The method of claim 3, wherein the PI3 kinase inhibitor is idelalisib.

7. The method of claim 3, wherein the PI3 kinase inhibitor is duvelisib.

8. The method of claim 3, wherein the PI3 kinase inhibitor is selected from the group consisting of wortmannin, demethoxyviridin, perifosine, buparlisib, copanlisib, and alpelisib.

9. The method of claim 1, wherein the PI3 kinase inhibitor is idelalisib.

10. The method of claim 1, wherein the PI3 kinase inhibitor is duvelisib.

11. The method of claim 1, wherein the PI3 kinase inhibitor is selected from the group consisting of wortmannin, demethoxyviridin, perifosine, buparlisib, copanlisib, and alpelisib.

12. The method of claim 1, wherein the anti-CD3 antibodies and anti-CD28 antibodies are immobilized on a bead or solid surface.

13. The method of claim 3, wherein the anti-CD3 antibodies and anti-CD28 antibodies are immobilized on a bead or solid surface.

* * * * *

SEQUENCE LISTING

```
<160> NUMBER OF SEQ ID NOS: 12

<210> SEQ ID NO 1
<211> LENGTH: 28
<212> TYPE: PRT
<213> ORGANISM: Artificial
<220> FEATURE:
<223> OTHER INFORMATION: Synthetic

<400> SEQUENCE: 1

Lys Pro Arg Arg Pro Tyr Thr Asp Asn Tyr Thr Arg Leu Arg Lys Gln
1               5                   10                  15

Met Ala Val Lys Lys Tyr Leu Asn Ser Ile Leu Asn
            20                  25

<210> SEQ ID NO 2
<211> LENGTH: 136
<212> TYPE: PRT
<213> ORGANISM: Artificial
<220> FEATURE:
<223> OTHER INFORMATION: Synthetic

<400> SEQUENCE: 2
```

```
Met Leu Leu Lys Leu Lys Glu Lys Ala Ser Leu Thr Leu Ala Val Gly
1               5                   10                  15

Thr Leu Pro Phe Pro Ser Gln Phe Asn Phe Val Pro Pro Gly Arg Met
            20                  25                  30

Cys Arg Val Ala Gly Trp Gly Arg Thr Gly Val Leu Lys Pro Gly Ser
            35                  40                  45

Asp Thr Leu Gln Glu Val Lys Leu Arg Leu Met Asp Pro Gln Ala Cys
        50                  55                  60

Ser His Phe Arg Asp Phe Asp His Asn Leu Gln Leu Cys Val Gly Asn
65                  70                  75                  80

Pro Arg Lys Thr Lys Ser Ala Phe Lys Gly Asp Ser Gly Gly Pro Leu
            85                  90                  95

Leu Cys Ala Gly Val Ala Gln Gly Ile Val Ser Tyr Gly Arg Ser Asp
            100                 105                 110

Ala Lys Pro Pro Ala Val Phe Thr Arg Ile Ser His Tyr Arg Pro Trp
            115                 120                 125

Ile Asn Gln Ile Leu Gln Ala Asn
        130                 135

<210> SEQ ID NO 3
<211> LENGTH: 697
<212> TYPE: PRT
<213> ORGANISM: Artificial
<220> FEATURE:
<223> OTHER INFORMATION: Synthetic

<400> SEQUENCE: 3

Asp Gly Ile Cys Lys Ser Ser Asp Cys Ile Lys Ser Ala Ala Arg Leu
1               5                   10                  15

Ile Gln Asn Met Asp Ala Thr Thr Glu Pro Cys Thr Asp Phe Phe Lys
            20                  25                  30

Tyr Ala Cys Gly Gly Trp Leu Lys Arg Asn Val Ile Pro Glu Thr Ser
            35                  40                  45

Ser Arg Tyr Gly Asn Phe Asp Ile Leu Arg Asp Glu Leu Glu Val Val
        50                  55                  60

Leu Lys Asp Val Leu Gln Glu Pro Lys Thr Glu Asp Ile Val Ala Val
65                  70                  75                  80

Gln Lys Ala Lys Ala Leu Tyr Arg Ser Cys Ile Asn Glu Ser Ala Ile
            85                  90                  95

Asp Ser Arg Gly Gly Glu Pro Leu Leu Lys Leu Leu Pro Asp Ile Tyr
            100                 105                 110

Gly Trp Pro Val Ala Thr Glu Asn Trp Glu Gln Lys Tyr Gly Ala Ser
            115                 120                 125

Trp Thr Ala Glu Lys Ala Ile Ala Gln Leu Asn Ser Lys Tyr Gly Lys
        130                 135                 140

Lys Val Leu Ile Asn Leu Phe Val Gly Thr Asp Asp Lys Asn Ser Val
145                 150                 155                 160

Asn His Val Ile His Ile Asp Gln Pro Arg Leu Gly Leu Pro Ser Arg
            165                 170                 175

Asp Tyr Tyr Glu Cys Thr Gly Ile Tyr Lys Glu Ala Cys Thr Ala Tyr
            180                 185                 190

Val Asp Phe Met Ile Ser Val Ala Arg Leu Ile Arg Gln Glu Glu Arg
            195                 200                 205

Leu Pro Ile Asp Glu Asn Gln Leu Ala Leu Glu Met Asn Lys Val Met
        210                 215                 220
```

```
Glu Leu Glu Lys Glu Ile Ala Asn Ala Thr Ala Lys Pro Glu Asp Arg
225                 230                 235                 240

Asn Asp Pro Met Leu Leu Tyr Asn Lys Met Thr Leu Ala Gln Ile Gln
            245                 250                 255

Asn Asn Phe Ser Leu Glu Ile Asn Gly Lys Pro Phe Ser Trp Leu Asn
        260                 265                 270

Phe Thr Asn Glu Ile Met Ser Thr Val Asn Ile Ser Ile Thr Asn Glu
    275                 280                 285

Glu Asp Val Val Tyr Ala Pro Glu Tyr Leu Thr Lys Leu Lys Pro
290                 295                 300

Ile Leu Thr Lys Tyr Ser Ala Arg Asp Leu Gln Asn Leu Met Ser Trp
305                 310                 315                 320

Arg Phe Ile Met Asp Leu Val Ser Ser Leu Ser Arg Thr Tyr Lys Glu
            325                 330                 335

Ser Arg Asn Ala Phe Arg Lys Ala Leu Tyr Gly Thr Thr Ser Glu Thr
        340                 345                 350

Ala Thr Trp Arg Arg Cys Ala Asn Tyr Val Asn Gly Asn Met Glu Asn
    355                 360                 365

Ala Val Gly Arg Leu Tyr Val Glu Ala Ala Phe Ala Gly Glu Ser Lys
370                 375                 380

His Val Glu Asp Leu Ile Ala Gln Ile Arg Glu Val Phe Ile Gln
385                 390                 395                 400

Thr Leu Asp Asp Leu Thr Trp Met Asp Ala Glu Thr Lys Lys Arg Ala
            405                 410                 415

Glu Glu Lys Ala Leu Ala Ile Lys Glu Arg Ile Gly Tyr Pro Asp Asp
        420                 425                 430

Ile Val Ser Asn Asp Asn Lys Leu Asn Asn Glu Tyr Leu Glu Leu Asn
    435                 440                 445

Tyr Lys Glu Asp Glu Tyr Phe Glu Asn Ile Ile Gln Asn Leu Lys Phe
450                 455                 460

Ser Gln Ser Lys Gln Leu Lys Lys Leu Arg Glu Lys Val Asp Lys Asp
465                 470                 475                 480

Glu Trp Ile Ser Gly Ala Ala Val Val Asn Ala Phe Tyr Ser Ser Gly
            485                 490                 495

Arg Asn Gln Ile Val Phe Pro Ala Gly Ile Leu Gln Pro Pro Phe Phe
        500                 505                 510

Ser Ala Gln Gln Ser Asn Ser Leu Asn Tyr Gly Gly Ile Gly Met Val
    515                 520                 525

Ile Gly His Glu Ile Thr His Gly Phe Asp Asp Asn Gly Arg Asn Phe
530                 535                 540

Asn Lys Asp Gly Asp Leu Val Asp Trp Trp Thr Gln Ser Ala Ser
545                 550                 555                 560

Asn Phe Lys Glu Gln Ser Gln Cys Met Val Tyr Gln Tyr Gly Asn Phe
            565                 570                 575

Ser Trp Asp Leu Ala Gly Gly Gln His Leu Asn Gly Ile Asn Thr Leu
        580                 585                 590

Gly Glu Asn Ile Ala Asp Asn Gly Gly Leu Gly Gln Ala Tyr Arg Ala
    595                 600                 605

Tyr Gln Asn Tyr Ile Lys Lys Asn Gly Glu Glu Lys Leu Leu Pro Gly
610                 615                 620

Leu Asp Leu Asn His Lys Gln Leu Phe Phe Leu Asn Phe Ala Gln Val
625                 630                 635                 640
```

```
Trp Cys Gly Thr Tyr Arg Pro Glu Tyr Ala Val Asn Ser Ile Lys Thr
            645                 650                 655

Asp Val Glu Ser Pro Gly Asn Phe Arg Ile Ile Gly Thr Leu Gln Asn
        660                 665                 670

Ser Ala Glu Phe Ser Glu Ala Phe His Cys Arg Lys Asn Ser Tyr Met
    675                 680                 685

Asn Pro Glu Lys Lys Cys Arg Val Trp
690                 695

<210> SEQ ID NO 4
<211> LENGTH: 29
<212> TYPE: PRT
<213> ORGANISM: Artificial
<220> FEATURE:
<223> OTHER INFORMATION: Synthetic

<400> SEQUENCE: 4

Tyr Phe Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg
            20                  25

<210> SEQ ID NO 5
<211> LENGTH: 23
<212> TYPE: PRT
<213> ORGANISM: Artificial
<220> FEATURE:
<223> OTHER INFORMATION: Synthetic

<400> SEQUENCE: 5

Phe Thr Asp Asn Tyr Thr Arg Leu Arg Lys Gln Met Ala Val Lys Lys
1               5                   10                  15

Tyr Leu Asn Ser Ile Leu Asn
            20

<210> SEQ ID NO 6
<211> LENGTH: 28
<212> TYPE: PRT
<213> ORGANISM: Artificial
<220> FEATURE:
<223> OTHER INFORMATION: Synthetic

<400> SEQUENCE: 6

His Ser Asp Ala Val Phe Thr Asp Asn Tyr Thr Arg Leu Arg Lys Gln
1               5                   10                  15

Leu Ala Val Lys Lys Tyr Leu Asn Ser Ile Leu Asn
            20                  25

<210> SEQ ID NO 7
<211> LENGTH: 6
<212> TYPE: PRT
<213> ORGANISM: Artificial
<220> FEATURE:
<223> OTHER INFORMATION: Synthetic

<400> SEQUENCE: 7

Lys Pro Arg Arg Pro Tyr
1               5

<210> SEQ ID NO 8
<211> LENGTH: 22
<212> TYPE: PRT
<213> ORGANISM: Artificial
<220> FEATURE:
```

```
<223> OTHER INFORMATION: Synthetic

<400> SEQUENCE: 8

Thr Asp Asn Tyr Thr Arg Leu Arg Lys Gln Met Ala Val Lys Lys Tyr
1               5                   10                  15

Leu Asn Ser Ile Leu Asn
            20

<210> SEQ ID NO 9
<211> LENGTH: 28
<212> TYPE: PRT
<213> ORGANISM: Artificial
<220> FEATURE:
<223> OTHER INFORMATION: Synthetic
<220> FEATURE:
<221> NAME/KEY: X
<222> LOCATION: (1)..(28)
<223> OTHER INFORMATION: X is norleucine

<400> SEQUENCE: 9

Lys Pro Arg Arg Pro Tyr Thr Asp Asn Tyr Thr Arg Leu Arg Lys Gln
1               5                   10                  15

Xaa Ala Val Lys Lys Tyr Leu Asn Ser Ile Leu Asn
            20                  25

<210> SEQ ID NO 10
<211> LENGTH: 27
<212> TYPE: PRT
<213> ORGANISM: Artificial
<220> FEATURE:
<223> OTHER INFORMATION: Synthetic

<400> SEQUENCE: 10

His Phe Asp Ala Val Phe Thr Asn Ser Tyr Arg Lys Val Leu Lys Arg
1               5                   10                  15

Leu Ser Ala Arg Lys Leu Leu Gln Asp Ile Leu
            20                  25

<210> SEQ ID NO 11
<211> LENGTH: 32
<212> TYPE: PRT
<213> ORGANISM: Artificial
<220> FEATURE:
<223> OTHER INFORMATION: Synthetic

<400> SEQUENCE: 11

Thr Asp Ser Tyr Ser Arg Tyr Arg Lys Gln Met Ala Val Lys Lys Tyr
1               5                   10                  15

Leu Ala Ala Val Leu Gly Lys Arg Tyr Lys Gln Arg Val Lys Asn Lys
            20                  25                  30

<210> SEQ ID NO 12
<211> LENGTH: 28
<212> TYPE: PRT
<213> ORGANISM: Artificial
<220> FEATURE:
<223> OTHER INFORMATION: Synthetic

<400> SEQUENCE: 12

His Ser Asp Ala Val Phe Thr Asp Asn Tyr Thr Arg Leu Arg Lys Gln
1               5                   10                  15

Met Ala Val Lys Lys Tyr Leu Asn Ser Ile Leu Asn
            20                  25
```